(12) United States Patent
Sharp

(10) Patent No.: US 11,229,580 B1
(45) Date of Patent: Jan. 25, 2022

(54) SECURING A PERCUTANEOUS FEEDING DEVICE

(71) Applicant: Meredith I. Sharp, Purcell, OK (US)

(72) Inventor: Meredith I. Sharp, Purcell, OK (US)

( * ) Notice: Subject to any disclaimer, the term of this patent is extended or adjusted under 35 U.S.C. 154(b) by 0 days.

(21) Appl. No.: 17/111,727

(22) Filed: Dec. 4, 2020

(51) Int. Cl.
*A61J 15/00* (2006.01)
*A61L 26/00* (2006.01)
*A61M 25/02* (2006.01)

(52) U.S. Cl.
CPC ....... *A61J 15/0057* (2013.01); *A61J 15/0015* (2013.01); *A61J 15/0034* (2013.01); *A61L 26/008* (2013.01); *A61L 26/0009* (2013.01); *A61M 25/02* (2013.01); *A61M 2025/026* (2013.01); *A61M 2025/0253* (2013.01)

(58) Field of Classification Search
CPC .......... A61M 25/02; A61M 2025/0253; A61M 2025/26; A61J 15/0057; A61J 15/0015; A61J 15/0034; A61J 26/0009; A61J 26/008
See application file for complete search history.

(56) References Cited

U.S. PATENT DOCUMENTS

| | | | |
|---|---|---|---|
| 5,092,850 A | 3/1992 | Burna | |
| 5,248,302 A | 9/1993 | Patrick et al. | |
| 5,484,420 A | 1/1996 | Russo | |
| 5,549,657 A | 8/1996 | Stern et al. | |
| 6,019,746 A | 2/2000 | Picha et al. | |
| 6,045,536 A | 4/2000 | Meier et al. | |
| 6,375,231 B1 | 4/2002 | Picha et al. | |
| 7,070,587 B2 | 7/2006 | Meier et al. | |
| 9,572,752 B1* | 2/2017 | Garcia ............... | A61J 15/0069 |
| 10,058,693 B2 | 8/2018 | Phillips et al. | |
| 10,492,999 B2 | 12/2019 | El-Haddad | |
| 10,517,754 B2 | 12/2019 | Pramme et al. | |
| 2003/0032932 A1* | 2/2003 | Stout ....................... | A61F 13/36 |
| | | | 604/385.01 |
| 2004/0186461 A1 | 9/2004 | DiMatteo | |
| 2006/0004345 A1 | 1/2006 | McMichael | |
| 2006/0095008 A1* | 5/2006 | Lampropoulos ...... | A61M 25/02 |
| | | | 604/174 |
| 2008/0097334 A1* | 4/2008 | Dikeman ............... | A61M 25/02 |
| | | | 604/180 |
| 2011/0118670 A1* | 5/2011 | Kay ....................... | A61M 25/02 |
| | | | 604/177 |
| 2013/0289486 A1 | 10/2013 | Evert et al. | |
| 2014/0142538 A1* | 5/2014 | Hyman ................ | A61F 13/0216 |
| | | | 604/500 |
| 2018/0296801 A1 | 10/2018 | Le et al. | |

* cited by examiner

*Primary Examiner* — Lauren P Farrar
(74) *Attorney, Agent, or Firm* — Hall Estill Law Firm

(57) ABSTRACT

Apparatus and associated methodology contemplating a securement device for securing a percutaneous feeding device having a tube operably forming a feeding passage through a stoma placed in a patient. The securement device has an adhesive-backed substrate configured to operably adhere to the patient's skin around the stoma. A connector is selectively extendable relative to the substrate and selectively moveable between an unsecured mode and a secured mode, the connector in the unsecured mode clearingly disengaging the feeding device, and the connector in the secured mode configured to impart a securement force to the feeding device to restrict its movement relative to the stoma.

20 Claims, 5 Drawing Sheets

SECURING A PERCUTANEOUS FEEDING DEVICE

BACKGROUND

The present technology contemplates devices and related methodologies for securing a percutaneous feeding device to a user's body, to resist environmental forces that can cause painful and injurious movement of the feeding device relative to the user's stoma through which it passes. More particularly, but without limitation, this technology contemplates a securement device anchored to the user's skin and selectively attachable to the feeding device's external bolster to impart securement forces restricting movement of the bolster relative to the user's skin and, in turn, to the stoma.

Percutaneous feeding devices, such as gastrostomy and jejunostomy feeding devices, are commonly used to feed patients who are otherwise unable to eat on their own accord due to some handicap, illness, or injury. United States surgeons put in place hundreds of thousands of percutaneous tube feeding devices each year to provide lifesaving nutrition.

One challenge of using a percutaneous feeding device is maintaining its intended internal operation and position despite it being subjected at times to harsh external environmental forces and impacts. A gastrostomy tube feeding device, for instance, is placed by inserting an internal end of it through an abdominal stoma and into the user's stomach. The internal end is secured inside the stomach by actuating a mechanical element (such as a balloon or lever), enlarging it to a size that is not easily pulled back out through the stoma. The externally-exposed portion of the feeding device has a bolster forming an enlarged support surface contacting the user's skin around the stoma. Those opposing internal and external support forces, and friction of the stoma contacting the feeding device, are adequate to keep the outlet of a feeding passage inside the stomach when the user is sedentary.

But common external environmental forces and impacts can defeat the feeding device's intended purpose, and cause further pain and injury. That is, it's possible for an accident, like a patient fall or caught up tubing, to cause impacts great enough to dislodge the feeding device out of its intended, operational position. Such impacts also cause serious compound effects too, such as internal lacerations, dehiscence, infection, swelling, pain, even organ obstructions, and like types of internal injury.

Some of these external forces and impacts are self-inflicted by the user, particularly where the user (patient) is unable to remain in a sedentary state for an extended period of time. Newborns, infants, and some adults with deficiencies in consciousness or development, all have in common that when they thrash about in pain, anger, or confusion, for example, the circumstances present serious risks of disrupting their feeding devices and injuring themselves. Serious complications can follow, including leakage of internal secretions, skin excoriation, inflammation, infection, open wounds, organ prolapse, improper healing, bleeding, and starvation. Extreme complications can lead to gastric or intestinal obstruction, and severe pain.

Previous attempts have been made to safeguard a feeding device in view of these predictable risks. Generally, they seek to lend support to the externally-exposed portion of the feeding device. For the newborns and infants mentioned above, unfortunately, all too often the surgeon will deep-suture the feeding device to the user's body to help secure it in the proper position. This is usually inadequate for providing a long term solution, as the sutures tend to tear away and cause further complications like pain, inflammation, open wounds, trauma to skin, and infection. It is heartbreaking to witness a helpless newborn baby suffering the pain and secondary complications of these inadequate solutions.

Alternatively, there are other previously attempted solutions involving a variety of complex and interlocking component parts. These approaches, however, are typically limited by the need to use specially-made mating parts. That is, a particular manufacturer's feeding tube typically has interlocking features that can only be used with a subset of that manufacturer's feeding device offerings, and cannot be used at all with any other manufacturer's feeding devices. This dependency on special purpose components defeats the cost and efficiency benefits of using universally fitting feeding device components. Some of the interlocking features are so complex that they render the feeding device cost prohibitive.

Improvements are needed that afford simple, inexpensive, and universal means of securing a user's percutaneous feeding device relative to the stoma it passes through, and that do not also increase any risk of feeding passage occlusion or restriction. It is to those improvements that illustrative embodiments of the current technology are disclosed herein.

SUMMARY

Some embodiments of the claimed technology contemplate a securement device for securing a percutaneous feeding device having a tube operably forming a feeding passage through a stoma placed in a patient. The securement device comprises an adhesive-backed substrate configured to operably adhere to the patient's skin around the stoma. A strap is selectively extendable relative to the substrate and is configured to be operably trained over an external portion of the feeding device. A closure is operative to secure the strap relative to the substrate so that the strap's medial portion imparts a securement force to the feeding device to restrict movement of the feeding device relative to the stoma.

Some embodiments of this technology contemplate a method for securing a percutaneous feeding device having a tube operably forming a feeding passage through a stoma placed in a patient. The method includes: obtaining a securement device having a substrate defining a central opening and a cut extending along a cut line from the opening to a peripheral edge; passing an external portion of the feeding device along the cut and into the opening; aligning the opening with the stoma; adhering the substrate to the patient's skin with the external portion of the feeding device passing through the opening; training a strap around a second external portion of the feeding device; and securing the strap to impart a securement force to the feeding device, restricting movement of the feeding device relative to the stoma.

Some embodiments of this technology contemplate a securement device for securing a percutaneous feeding device having a tube operably forming a feeding passage through a stoma placed in a patient. The securement device has an adhesive-backed substrate configured to operably adhere to the patient's skin around the stoma. A connector is selectively extendable relative to the substrate and selectively moveable between an unsecured mode and a secured mode, the connector in the unsecured mode clearingly disengaging the feeding device, and the connector in the secured mode configured to impart a securement force to the feeding device to restrict its movement relative to the stoma.

DETAILED DESCRIPTION

Initially, this disclosure is by way of example only, not by limitation. The illustrative constructions and associated methods disclosed herein are not limited to use or application for clamping any specific workpiece, despite the application to a gastrostomy feeding device of a particular type and style in the disclosure of illustrative embodiments. Alternatively, the skilled artisan will recognize that the principles set forth in the illustrative embodiments of this disclosure can alternatively be achieved by modified constructions suitable for use with other types of percutaneous feeding devices and with other types of devices used in percutaneous procedures. Thus, although the instrumentalities described herein are for the convenience of explanation, shown and described with respect to exemplary embodiments, the skilled artisan understands that the operating principles for securing a percutaneous device as set forth herein are in no way limited by the specific disclosures of the exemplary embodiments.

Figure 1:
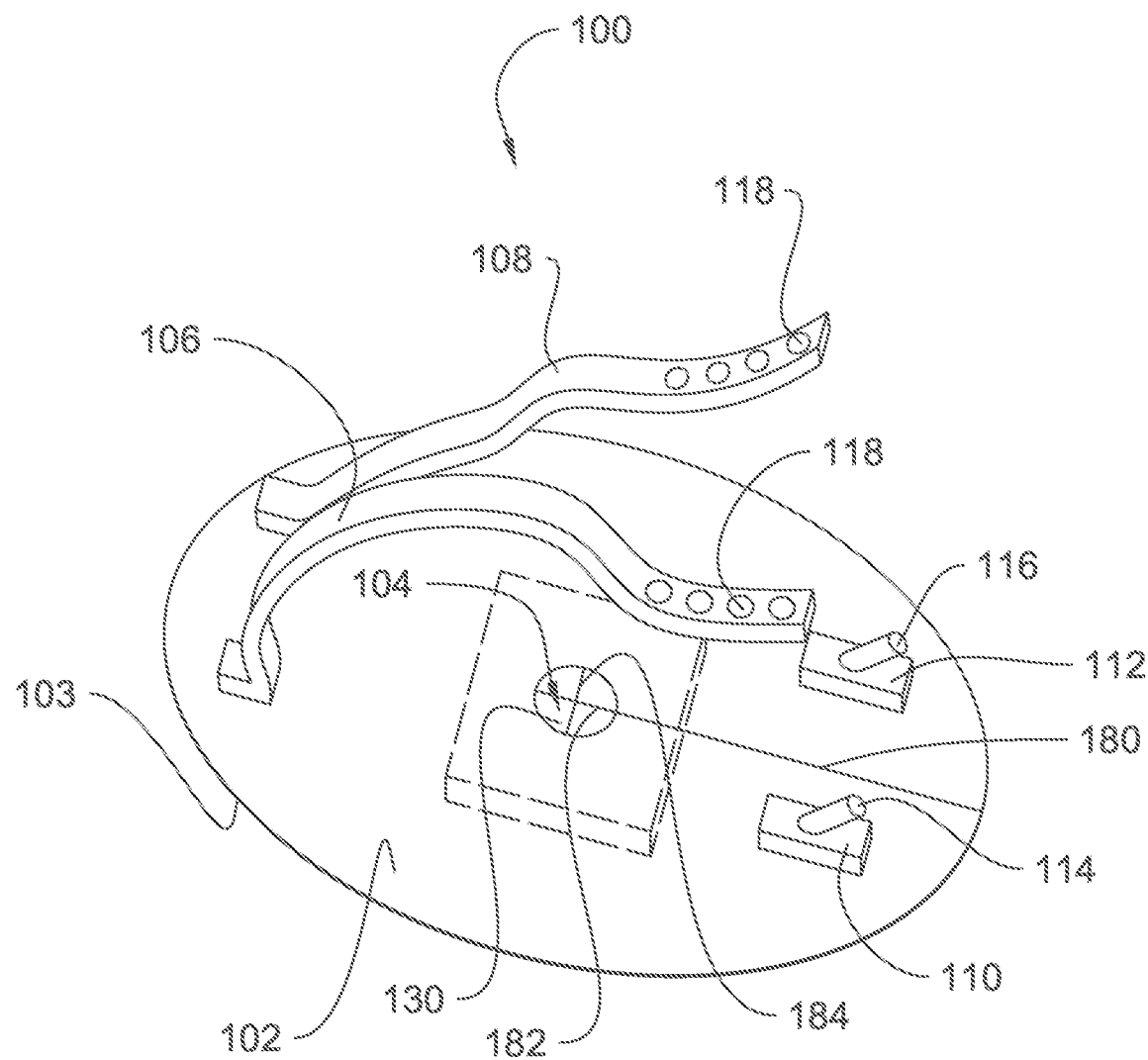
FIG. 1 is an isometric depiction of a securement device that is constructed in accordance with illustrative embodiments of this technology.

FIG. 1 is an isometric depiction of a securement device 100 that is constructed in accordance with illustrative embodiments of this technology for purposes of this detailed description. The securement device 100 is generally a thin flexible wafer that adheres to the user's skin between it and the external bolster portion of the feeding device, with attachment features for attaching the adhered wafer to external portions of the feeding device's bolster.

The illustrative securement device 100 in FIG. 1 has flexible substrate 102. An adhesive 103 can be applied to the exposed lower surface of the substrate 102, and a backing sheet (not depicted) can be used to protectively cover the adhesive 103 until it is time to adhere the device 100 to the user. A substrate made of a flexible material will closely conform to the patient's body, promoting adhesion and patient comfort. However, the flexible substrate of these illustrative embodiments is in no way limiting of the claimed technology, in that alternatively the substrate can be rigid or a combination of flexible portions and rigid portions. A rigid substrate, or portion, can is comparatively stronger and thus could provide more resistance to restrict movement of the feeding device.

In illustrative embodiments, the substrate 102 can be constructed from a hydrocolloid or silicone dressing in order to furnish therapeutic treatment to the skin surrounding the stoma. The substrate 102 defines a central opening 104 that is sized to clearingly disengage from the tubular portion of the feeding device extending between the user's stoma and the feeding device's external bolster.

Also depicted in the illustrative embodiments of FIG. 1, the securement device 100 has a pair of flexible straps 106, 108. Each strap 106, 108 depends from the substrate 102 at a proximal end, and has a freely positionable distal end in these illustrative embodiments. Once the securement device 100 has been adhered to the user's skin, then the straps 106, 108 can be selectively positioned to train their medial portions over external portions of the feeding device, such as over the bolster in the illustrative discussion below.

Although the straps are constructed of a flexible material in these illustrative embodiments, the claimed technology is not so limited. Alternative embodiments (not depicted) contemplate the straps can be constructed of a rigid material, or combination of flexible and rigid components without departing from the scope of the claimed technology.

The securement device 100 of FIG. 1 also has a closure 110, 112, each corresponding to one of the straps 106, 108. The closure 110, 112 secures the distal end of one of the straps 106, 108 after its medial portion has been trained over the external portion of the feeding device. This securement of the distal ends causes the medial portions of the straps 106, 108 to independently impart respective securement forces safeguarding the feeding device from adverse external environmental forces and impacts.

In these illustrative embodiments, each closure 110, 112 has a protuberant pin 114, 116 anchored in place relative to the substrate 102. Each strap 106, 108 forms one or more holes 118 that are sized to admit one of the protuberant pins 114, 116. Multiple holes 118 in each strap 106, 108 provide flexible strap length, such that they can be trained either parallel to each other or crossing each other, whichever is optimal, and then attached to the pins 114, 116.

Thus, to secure a strap 106, 108, the user selects the most appropriate one of the holes 118 to matingly engage with a respective one of the pins 114, 116. Where multiple holes 118 are provided on a strap 106,108, the most appropriate one is the one that provides the desired tautness to the strap 106, 108 passing over the external portion of the feeding device. A strap that is not taut at all will not transfer any securement force to the feeding device, whereas a strap that is too taut can cause pain and discomfort by pressing on the feeding device at all times.

Figure 2:
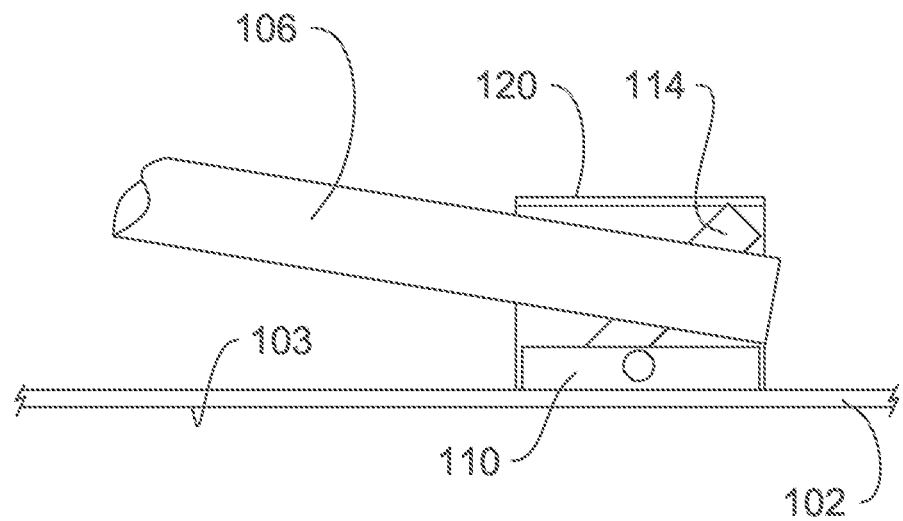
FIG. 2 is a simplified side depiction of the distal end of one of the securement straps in the secured mode.

FIG. 2 depicts a side view of the strap 106 in the secured mode, having its distal end secured to the pin 114. Note that in these illustrative embodiments the pin 114 is angled away from the strap 106, effectively hooking the strap's 106 distal end in the secured mode to lessen any likelihood that the strap 106 might inadvertently become unsecured by coming off the pin 114.

Figure 3:
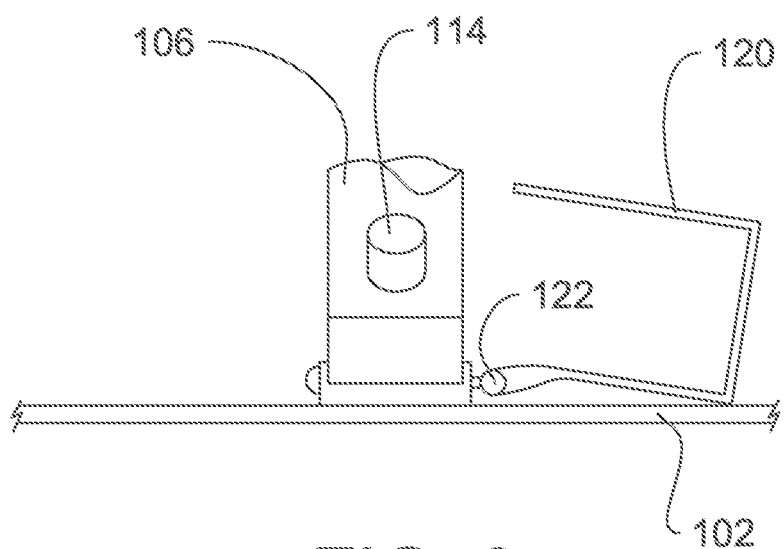
FIG. 3 is a simplified end depiction of FIG. 2.
Figure 4:
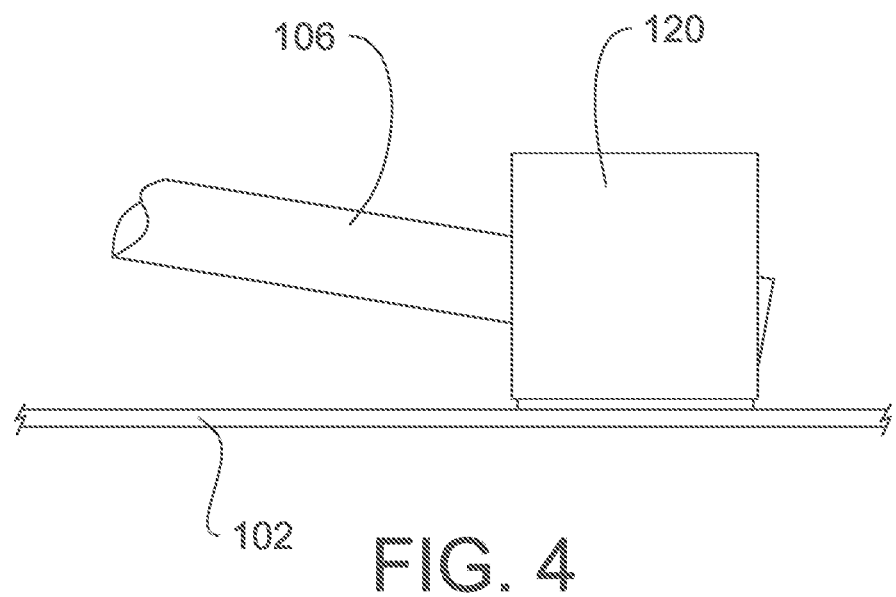
FIG. 4 is similar to FIG. 3 but depicting the cover in the closed position.
Figure 5:
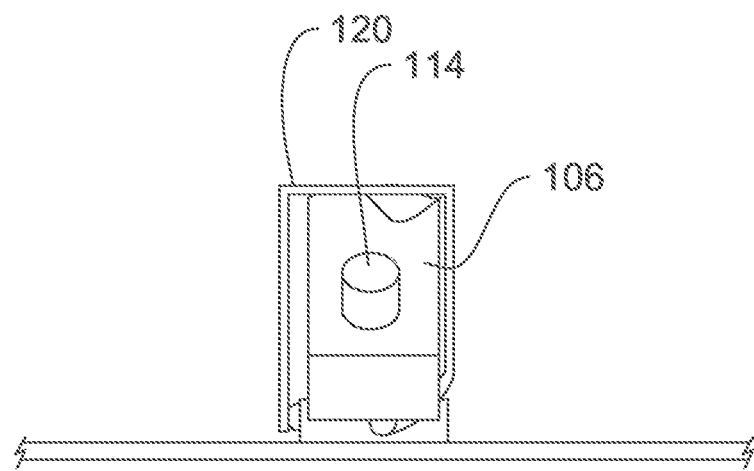
FIG. 5 is a simplified end depiction of FIG. 4.

Other measures can be taken to more affirmatively lock the strap 106, 108 to the closure member 110, 112 to prevent them from inadvertently becoming unsecured. Here and in FIG. 3 each closure member 110, 112 further has a cover 120, shown in the open position. FIGS. 4 and 5 are similar to FIGS. 2 and 3, but depict the cover 120 rotated to the closed position. In the closed position, the cover 120 blocks the free end of the pin 114 to prevent the strap 106 from inadvertently coming off it. That is, in these illustrative embodiments the strap 106 cannot come off the pin 114 if the cover 120 is closed, as depicted in FIGS. 4 and 5. Generally, the cover 120 can be selectively movable between an open position as depicted in FIGS. 2 and 3, unblocking the free end of the pin 114 so that the strap's 106 distal end can be operably placed onto and removed from the pin 114, and a closed position as depicted in FIGS. 4 and 5, blocking the free end of the pin 114 so that the strap's 106 distal end cannot under any circumstances be removed from the pin 114. In these illustrative embodiments the cover 120 is selectively rotatable between the open and closed positions by a hinge 122 connecting the closure 110 and the cover 120 together.

The opposing proximal ends of the straps 106, 108 are fixedly attached to the substrate 102 in these illustrative embodiments, such as by adhering them, fusing them, and the like. In alternative embodiments not depicted, the proximal ends of the straps and the substrate are unitarily constructed, such as by molding them together as one component part. In other alternative equivalent embodiments, not depicted, the straps can be entirely removable from the substrate. For instance, both ends of each strap can be configured to selectively engage a respective closure member in a manner similar to that described above.

Figure 6:
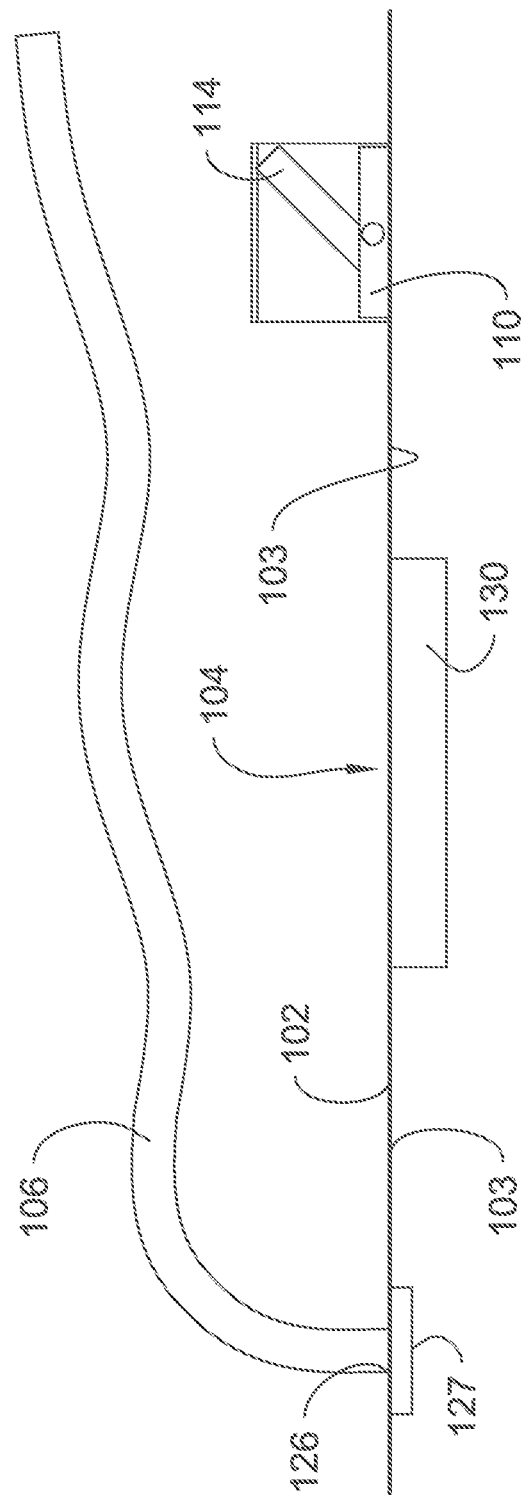
FIG. 6 depicts a simplified side elevational depiction of the securement device of FIG. 1.

FIG. 6 depicts yet further alternative embodiments in which the strap 106 passes through a clearance opening 126 in the substrate 102, and its proximal end has a flange 127 that is adhered to the underside of the substrate 102.

Figure 7:
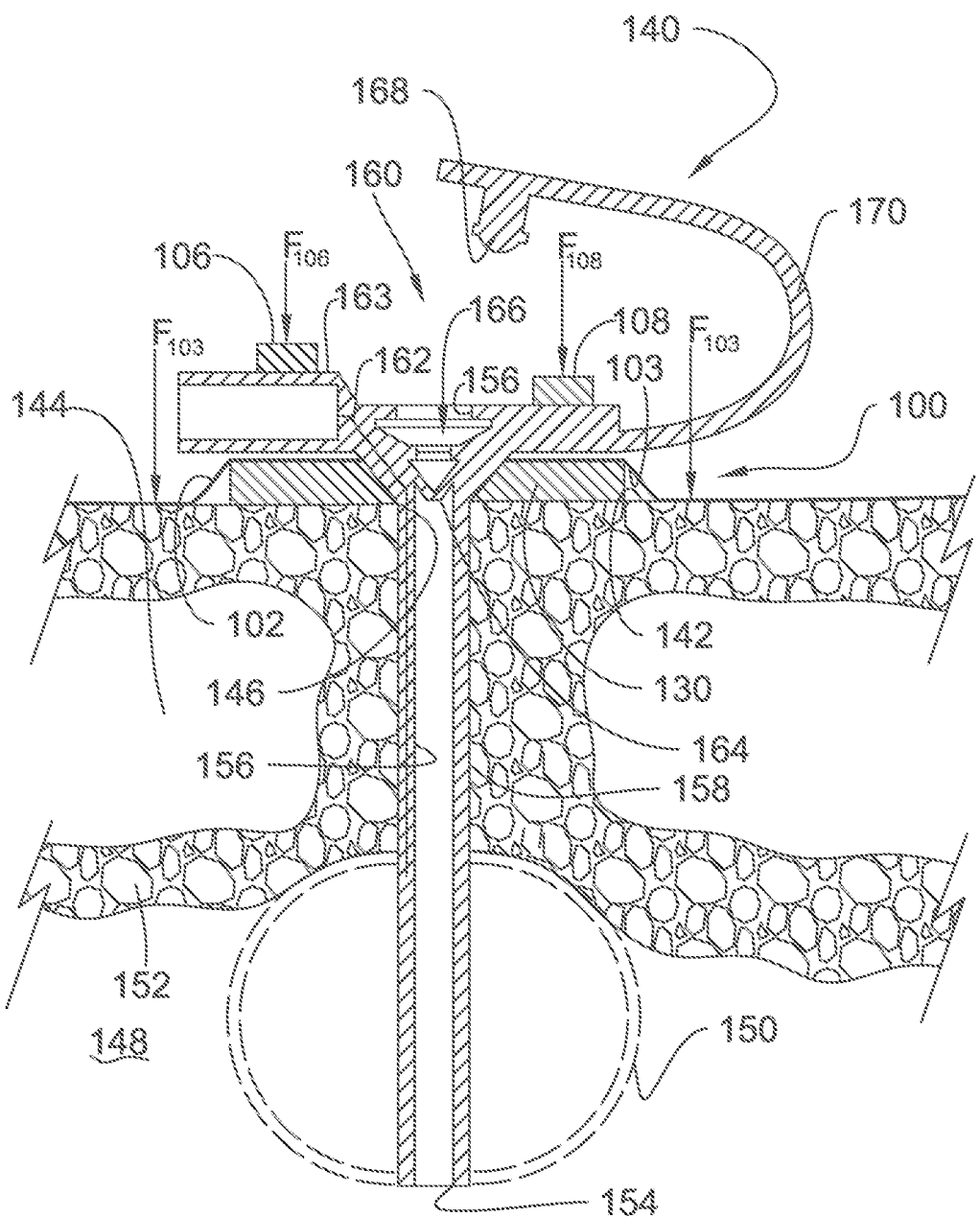
FIG. 7 is a simplified cross-sectional depiction of the securement device of FIG. 1 in operation securing a low profile feeding device to restrict its movement relative to the user's stoma.

FIGS. 1 and 7 best depict a dressing 130 can be provided between the substrate 102 and the exposed end of the user's stoma. In these illustrative embodiments the dressing 130 is adhered on its topside to the adhesive 103 on the underside of the substrate 102, so that the dressing's underside is operably pressed against the stoma by adhering the substrate 102 to the user's skin. Preferably, the dressing 130 can be made of a hydrophilic material to promote the desired wound healing conditions by absorbing any wound exudate from the user's stoma. The thickness of such a dressing, being significantly greater than the substrate, also advantageously provides a cushioning barrier protectively covering the stoma during the healing from surgery. Such a hydrophilic dressing 130 can be constructed, for example, by using a product marketed under the Mepilex® brand by Mölnlycke Health Care having United States offices in Peachtree Corners, Ga.

FIG. 7 diagrammatically depicts the securement device 100 described above as it is operably adhered to the user's abdomen directly under the externally-exposed portion of a gastrostomy feeding device 140. As described above, the feeding device 140 has been inserted through a stoma 146 placed in the user's abdominal wall 144, and the internal end of the feeding device 140 has further been inserted into the stomach 148. A balloon 150 has been inflated to enlarge it to a size that cannot readily be pulled back out through the stoma 146. The inflated balloon 150 urges the stomach wall 152 against the abdominal wall 144, and thereby secures a feeding passage outlet 154 to remain situated inside the stomach 148. Thus, food from a feeding tube (not depicted) that is connected to a feeding passage inlet 156 will be delivered through the feeding passage and into the user's stomach.

The feeding device 140 depicted in FIG. 7 is commonly referred to as a low profile, button type of feeding device using balloon stabilization. Although the claimed embodiments are well suited for use with this type of low profile feeding device, the claimed embodiments are not so limited. The embodiments of this technology can alternatively be used to secure the externally-exposed portion of any other type of percutaneous device as well.

The feeding device 140 generally has an elongated tubular member 158 extending from a bolster portion 160. The tubular member 158 defines the feeding passage 156, and also defines an inflation passage 162 for admitting and releasing a pressurized fluid (such as sterile or distilled water) to inflate and deflate the balloon 150, respectively. The inflation passage 162 extends between an inflation housing 163 and the interior space of the balloon 150.

Both the feeding passage 156 and the inflation passage 162 extend through the bolster 160 in these illustrative embodiments. A duckbill type check valve 164 prevents flow of the food out of the inlet end of the food passage 156. Above the check valve 164, the inlet 156 defines a cavity 166 that is shaped to mate with a locking cap 168. The cap 168 is tethered to the bolster 160 by a flexible strap 170.

FIG. 7 is a simplified cross-sectional depiction of the securement device 100 in its intended operation of securing the bolster 160, and thereby restricting its movement relative to the user's stoma 146. The substrate 102 is adhered to the user's epidermal surface 142 between it and the bolster 160, and surrounding the stoma 146. This adhesive force, depicted as force arrows FHB acting throughout the area of the adhesive 103, immobilizes the substrate 102 relative to the stoma 146. The straps 106, 108 are trained over the bolster 160 and secured at their distal ends. The securement forces imparted by medial portions of the straps 106, 108, depicted as force arrows $F_{106}$ and $F_{108}$, immobilize the bolster 160 relative to the substrate 102 and, in turn, relative to the stoma 146 by way of the adhesion of the substrate 102 to the user's skin 142 surrounding the stoma 146.

Note that the strap 106 is trained over the inflation housing 163, which is higher than the portion of the bolster 160 that the other strap 108 is trained over. Compensating the strap length for different heights of the bolster 160 can be accomplished by constructing the straps of an elastic material affording some amount of stretching, and by providing the multiple attachment holes 118 (FIG. 1) as discussed above in these illustrative embodiments, and the like. Also as discussed above, instead of training the medial portions of the straps 106, 108 in parallel with each other as depicted in FIG. 7, they could instead be crossed with respect to each other if that provided a better application of the intended securement forces to the feeding device 140.

The securement device 100 must be capable of being attached to and removed from the user without disturbing the placement of the feeding device 140 in the user's stoma 146. To accomplish that, referring back to FIG. 1, the substrate 102 is cut from its central opening 104 to the outer edge, making it separable along the cut 180. The dressing 130 is likewise cut, making it separable along a cut 182 that is aligned with the substrate's cut 180. In these illustrative embodiments the dressing 130 also has a perpendicular cut 184 intersecting the dressing's other cut 182 at the center of the substrate's opening 104.

So to attach the securement device 100, before removing the protective backing sheet from the adhesive 103 on the underside of the substrate 102, the substrate 102 and dressing 130 are spread apart along the aligned cut lines 180, 182 to create an enlarged radially-directed opening in the substrate 102 and dressing 130. Aligning this radial opening with the central portion of the bolster 160 between it and the user's skin surface 142, and moving the substrate 102 laterally so that the bolster 160 traverses the radial opening, permits moving the substrate 102 into its operational position placed around the stoma 146. The dressing 130 separates along its cut lines 182, 184 to provide clearance for the central portion of the bolster 160 passing through the substrate's opening 104. The backing sheet (not depicted) can then be removed to adhere the substrate 102 to the user's skin 142 at the operational position.

The various features and alternative details of construction described herein for the practice of the present technology will readily occur to the skilled artisan in view of the foregoing discussion, and it is to be understood that even though numerous characteristics and advantages of various embodiments of the present technology have been set forth in the foregoing description, together with details of the structure and function of various embodiments of the technology, this detailed description is illustrative only, and changes may be made in detail, especially in matters of structure and arrangements of parts within the principles of the present technology to the full extent indicated by the broad general meaning of the terms in which the appended claims are expressed.

What is claimed:

1. A securement device for securing a percutaneous feeding device having a tube terminating at an external bolster, the tube and bolster cooperatively configured for forming a feeding passage through a stoma placed in a patient, the securement device comprising:
    a substrate configured to be operably adhered to the patient's skin around the stoma;
    a strap operably extendable from a first portion of the substrate adjacent skin on a first side of the stoma, and the strap further having a medial portion configured to be operably trained over the bolster portion of the feeding device; and
    a closure to operably secure the strap relative to a second different portion of the substrate adjacent skin on a different second side of the stoma so that the strap and, in turn the substrate, impart securement forces anchoring the feeding device to skin on two different sides of the stoma to restrict movement of the feeding device relative to the stoma.

2. The securement device of claim 1 wherein the substrate comprises a hydrocolloid dressing.

3. The securement device of claim 1 wherein the substrate comprises a silicone dressing.

4. The securement device of claim 1 wherein the strap is connected to the substrate.

5. The securement device of claim 4 wherein the strap is removably connectable to the substrate.

6. The securement device of claim 5 wherein the strap defines an opening, and wherein the closure comprises a protuberant member sized to be inserted in the opening to affix the strap over the feeding device in a secured mode.

7. The securement device of claim 6 comprising two straps each operably imparting securement forces securing the feeding device.

8. The securement device of claim 6 further comprising a cover selectively operable to block a free end of the protuberant member to retain the strap operably affixed over the feeding device.

9. The securement device of claim 8 wherein at least a portion of the cover is selectively rotatable with respect to the pin.

10. The securement device of claim 1 wherein the substrate defines a stoma opening through which the feeding device extends from the stoma.

11. The securement device of claim 10 comprising two straps on opposing sides of the stoma opening.

12. The securement device of claim 11 wherein the substrate defines a passageway extending from the opening to a peripheral edge and configured to admit a portion of the external portion.

13. The securement device of claim 12 further comprising a hydrophilic dressing supported by the substrate and aligned with the stoma opening.

14. The securement device of claim 13 wherein the hydrophilic dressing defines a cut aligned with the substrate's passageway.

15. A method for securing a percutaneous feeding device having a tube terminating at an operably exposed external portion, the tube and external portion cooperatively configured for forming a feeding passage through a stoma placed in a patient, the method comprising:
    obtaining a securement device having a substrate defining an opening and a passageway extending from the opening to a peripheral edge;
    moving the securement device relative to the stoma, by admitting the external portion of the feeding device into the passageway;
    further moving the securement device relative to the stoma to align the opening with the stoma, so that the exposed external portion extends out of the stoma and through the opening;
    adhering the aligned substrate to the patient's skin;
    training a strap around the external portion of the feeding device; and
    securing the strap to the substrate, imparting a securement force to the feeding device to restrict its movement relative to the stoma.

16. A securement device for securing a percutaneous feeding device having a tube terminating at an external bolster, the tube and bolster cooperatively configured for forming a feeding passage through a stoma placed in a patient, the securement device comprising:
    a substrate configured to be operably adhered to the patient's skin around the stoma; and
    a pair of connectors each extending from the substrate and individually moveable between an unsecured mode and a secured mode, each connector individually in the unsecured mode clearingly disengaging the feeding device, and each connector individually in the secured mode configured to impart securement forces anchoring the feeding device to skin, so that when both connectors are secured, they impart the securement forces on two different sides of the stoma to restrict movement of the feeding device relative to the stoma.

17. The securement device of claim 16, wherein at least one of the connectors comprises:
    a strap configured to be operably trained over an external portion of the feeding device; and
    a closure selectively operable to affix the strap relative to the substrate in the secured mode, imparting the securement force to the feeding device to restrict its movement relative to the stoma.

18. The securement device of claim 17 wherein the strap is constructed of a flexible material.

19. The securement device of claim 16 wherein the substrate defines an opening, the feeding device extending out of the stoma and through the opening, and further comprising a dressing covering the opening.

20. A securement device for securing a percutaneous feeding device having a tube operably forming a feeding passage through a stoma placed in a patient, the securement device comprising:
    a substrate configured to be operably attached to the patient's skin around the stoma, the substrate defining a stoma opening configured to clearingly receive an external portion of the feeding device extending out of the stoma, and the substrate further defining a passage extending from the stoma opening to a peripheral edge of the substrate;

a hydrophilic dressing supported by the substrate, the hydrophilic dressing having a cut aligned with the substrate's passage;

a pair of straps, each individually extendable relative to the substrate and configured to be individually trained over the external portion of the feeding device; and a pair of closures, each configured to individually secure a selected one of the straps relative to the substrate so that the selected strap imparts a securement force to the feeding device to restrict movement of the feeding device relative to the stoma.

\* \* \* \* \*